(12) United States Patent
Fishel

(10) Patent No.: US 9,352,159 B2
(45) Date of Patent: May 31, 2016

(54) CARDIAC RESYNCHRONIZATION THERAPY UTILIZING P-WAVE SENSING AND DYNAMIC ANTICIPATIVE LEFT VENTRICULAR PACING

(71) Applicant: NewPace Ltd., Caesarea (IL)

(72) Inventor: Robert S. Fishel, Delray Beach, FL (US)

(73) Assignee: NewPace Ltd., Caesarea (IL)

( * ) Notice: Subject to any disclaimer, the term of this patent is extended or adjusted under 35 U.S.C. 154(b) by 0 days.

(21) Appl. No.: 14/783,279

(22) PCT Filed: Apr. 9, 2014

(86) PCT No.: PCT/IL2014/050345
§ 371 (c)(1),
(2) Date: Oct. 8, 2015

(87) PCT Pub. No.: WO2014/167568
PCT Pub. Date: Oct. 16, 2014

(65) Prior Publication Data
US 2016/0045736 A1 Feb. 18, 2016

Related U.S. Application Data

(60) Provisional application No. 61/809,936, filed on Apr. 9, 2013.

(51) Int. Cl.
*A61N 1/362* (2006.01)
*A61N 1/368* (2006.01)
*A61N 1/05* (2006.01)
*A61N 1/365* (2006.01)
*A61N 1/375* (2006.01)
*A61B 5/0452* (2006.01)

(52) U.S. Cl.
CPC ............ *A61N 1/3682* (2013.01); *A61N 1/0587* (2013.01); *A61N 1/3684* (2013.01); *A61N 1/36514* (2013.01); *A61N 1/375* (2013.01); *A61B 5/0452* (2013.01)

(58) Field of Classification Search
CPC . A61N 1/3682; A61N 1/3684; A61N 1/0587; A61N 1/375; A61N 1/36514; A61B 5/0452
USPC .................. 607/17, 18, 25; 600/516, 517, 519
See application file for complete search history.

(56) References Cited

U.S. PATENT DOCUMENTS

| 6,556,859 B1 | 4/2003 | Wohlgemuth et al. |
| 8,160,700 B1 | 4/2012 | Ryu et al. |

(Continued)

OTHER PUBLICATIONS

The International Preliminary Report on Patentability for International Application No. PCT/IL2014/050345, Mailed Aug. 30, 2015, 5 pages.

(Continued)

*Primary Examiner* — Theodore Stigell
*Assistant Examiner* — Michael Carey
(74) *Attorney, Agent, or Firm* — Brown Rudnick LLP

(57) ABSTRACT

A method for operating a pacemaker comprises the procedures of building a database of a cardiac cycle of a patient suffering from bundle branch block and artificially pacing a ventricle of the patient using the pacemaker according to anticipative atrioventricular (AV) delays in the database which are based on measured P-P intervals in the database.

43 Claims, 7 Drawing Sheets

(56) References Cited

U.S. PATENT DOCUMENTS

| | | |
|---|---|---|
| 2002/0026220 A1 | 2/2002 | Groenewegen et al. |
| 2004/0215238 A1 | 10/2004 | van Dam et al. |
| 2005/0027321 A1 | 2/2005 | Ferek-Petric |
| 2010/0087888 A1 | 4/2010 | Maskara |
| 2011/0178567 A1* | 7/2011 | Pei .................. A61N 1/365 607/25 |
| 2013/0035738 A1 | 2/2013 | Karst et al. |

OTHER PUBLICATIONS

International Search Report and the Written Opinion for International Application No. PCT/IL2014/050345, mailed Aug. 31, 2014, 10 pages.

International Search Report for International Application No. PCT/IL2014/050345, mailed Aug. 31, 2014, 4 pages.

* cited by examiner

CARDIAC RESYNCHRONIZATION THERAPY UTILIZING P-WAVE SENSING AND DYNAMIC ANTICIPATIVE LEFT VENTRICULAR PACING

FIELD OF THE DISCLOSED TECHNIQUE

The disclosed technique relates to cardiac resynchronization therapy, in general, and to methods and systems for improved cardiac synchronization therapy using P-wave sensing and dynamic anticipative left ventricular pacing, in particular.

BACKGROUND OF THE DISCLOSED TECHNIQUE

The heart is the muscle in the body responsible for pumping and circulating blood throughout the body. The heart achieves this circulatory action by rhythmically contracting its inner and outer walls, thus pumping blood it receives throughout the body. The rhythmic contractions of the heart are initiated and controlled by electrical impulses (also referred to herein interchangeably as electrical signals or electrical charges) produced by special cells in the heart known as pacemaker cells. These cells form a network throughout various regions of the heart, creating what is referred to as the electrical conduction system of the heart. As an electrical impulse conducts through the electrical conduction system of the heart through various regions of the heart, these regions in turn contract thus pumping blood out of the heart. Reference is now made to FIG. 1A which is a schematic illustration of the major parts of a human heart, from a coronal cross-sectional view, generally referenced 10, and the electrical conduction system of heart 10, as is known in the prior art. Heart 10 is made up of four chambers, separated into a left side and a right side. Each of the left side and the right side of heart 10 respectively include two chambers. These chambers are a right atrium 12, a left atrium 14, a right ventricle 16 and a left ventricle 18. Right atrium 12 and right ventricle 16 are substantially coupled with one another however they are separated into two chambers by a set of valves 20, known collectively as the tricuspid valve (also referenced as tricuspid valve 20). Left atrium 14 and left ventricle 18 are also substantially coupled with one another however they are also separated into two chambers by a set of valves 22, known collectively as the mitral valve (also referenced as mitral valve 22). Both tricuspid valve 20 and mitral valve 22 are unidirectional valves, only allowing blood to flow from an atrium to a ventricle and thus preventing blood from flowing from a ventricle into an atrium. In normal, healthy human hearts, right atrium 12 and right ventricle 16 are completely sealed from left atrium 14 and left ventricle 18 by a wall 26, known as the septum (also referenced as septum 26).

Each side of the heart is responsible for pumping blood through a major loop or cycle in a body (not shown). The right side of the heart receives deoxygenated blood (not shown) from the body and pumps the deoxygenated blood to the lungs (not shown) where the blood is re-oxygenated. The left side of the heart receives the re-oxygenated blood (not shown) from the lungs and pumps the re-oxygenated blood to the body. Right atrium 12 receives deoxygenated blood from the body via the superior vena cava (not shown) and the inferior vena cava (not shown), which both empty the deoxygenated blood collected from all the cells and tissues of the body into right atrium 12. As right atrium 12 fills with blood, the deoxygenated blood is pushed through tricuspid valve 20 into right ventricle 16. Once right ventricle 16 is filled, it in turn pumps the deoxygenated blood into the pulmonary artery (not shown), which transports the deoxygenated blood to the lungs for re-oxygenation. Re-oxygenated blood is brought from the lungs to left atrium 14 via the pulmonary vein (not shown). As left atrium 14 fills with blood, the re-oxygenated blood is pushed through mitral valve 22 into left ventricle 18. Once left ventricle 18 is filled, it in turn pumps the re-oxygenated blood into the aorta (not shown), which transports the re-oxygenated blood to the cells and tissues of the body via a network of arteries. Right ventricle 16 and left atrium 14 thus form the pulmonary loop or cycle in the body as blood is transferred to and from heart 10 to the lungs. Right atrium 12 and left ventricle 18 thus form the circulatory loop or cycle in the body as blood is transferred to and from heart 10 to the cells and tissues of the body.

Heart 10 is substantially composed of two types of cells, known as myocardiocytes and pacemaker cells. Myocardiocytes are a type of involuntary muscle cell that can contract upon the reception of electrical impulses. Right atrium 12, left atrium 14, right ventricle 16 and right ventricle 18 (i.e., a majority of heart 10) are composed of a plurality of myocardiocytes 24, which all contract upon receiving electrical impulses. The contraction of myocardiocytes is what results in the pumping action of heart 10, thus enabling the atria (plural of atrium) of heart 10 to pump blood in the ventricles and enabling the ventricles to pump blood to the lungs and the rest of the body. As mentioned above, the pacemaker cells (not specifically referenced) are responsible to generating electrical impulses which travel through the various chambers of the heart, thus causing the pumping action of the heart.

The electrical conduction system of heart 10 includes a sinoatrial (herein abbreviated SA) node 28, an atrioventricular (herein abbreviated AV) node 30, an AV bundle 32 (also known as and referenced as bundle of HIS 32), a right bundle branch 34, a left bundle branch 36 and a plurality of fibers 38 (also known as and referenced as plurality of Purkinje fibers 38). Each one of SA node 28, AV node 30, bundle of HIS 32, right bundle branch 34, left bundle branch 36 and plurality of Purkinje fibers 38 is composed of pacemaker cells. Pacemaker cells are unique in that they can involuntarily and rhythmically produce electrical impulses and can also transfer electrical impulses they receive. In normal hearts, the pacemaker cells (not shown) in SA node 28 produce about 100 electrical impulses per minute, the pacemaker cells (not shown) in AV node 30 produce about 40-60 electrical impulses per minute and the pacemaker cells (not shown) in bundle of HIS 32, right bundle branch 34, left bundle branch 36 and plurality of Purkinje fibers 38 produce about 30-40 electrical impulses per minute. Since the pacemaker cells in SA node 28 produce electrical impulses quicker than any other area of heart 10, SA node 28 functions as the primary or normal pacemaker of heart 10. SA node 28 is located in right atrium 12 and is coupled with AV node 30 via the internodal tracts (not shown). AV node 30 is located in septum 26, right at the intersection of all the chambers of heart 10. Bundle of HIS 32 branches off from AV node 30 along septum 26 and splits into right bundle branch 34 and left bundle branch 36. Right bundle branch 34 lines the interior wall of right ventricle 16 whereas left bundle branch 36 lines the interior wall of left ventricle 18. The distal end (not labeled) of each of right bundle branch 34 and left bundle branch 36 branches off into a network of smaller pacemaker cells which form plurality of Purkinje fibers 38. Plurality of Purkinje fibers 38 also lines the interior walls of right ventricle 16 and left ventricle 18, in the direction towards right atrium 12 and left atrium 14 respectively.

Reference is now made to FIG. 1B which is a schematic illustration of the heart shown in FIG. 1A, from a coronal cross-sectional view, showing the flow of electrical impulses through the electrical conduction system of the heart, generally referenced 50, as is known in the prior art. Identical parts of heart 50 in FIG. 1B and heart 10 in FIG. 1A are labeled using equivalent reference numbers. In normal hearts (i.e., where the physiology of the heart is normal), SA node 28 initiates an electrical impulse (not labeled). The electrical impulse travels through right atrium 12 and left atrium 14, shown by a plurality of arrows 52. This traveling electrical impulse causes both right atrium 12 and left atrium 14 to contract simultaneously, thus causing blood to flow from right atrium 12 into right ventricle 16 and from left atrium 14 into left ventricle 18. The electrical impulse eventually reaches AV node 30 which causes a delay in the transfer of the electrical impulse to bundle of HIS 32. This delay is known as the AV delay (explained in more detail below in FIG. 2A) and substantially enables both atria to empty completely of blood. After the AV delay, AV node 30 transfers the electrical impulse to bundle of HIS 32, shown by an arrow 54. Bundle of HIS 32 in turn transfers the electrical impulse to right bundle branch 34, shown as a plurality of arrows 56 and left bundle branch 36, shown as a plurality of arrows 58, thus causing right ventricle 16 and left ventricle 18 respectively to begin contracting. The split electrical impulse is then transferred to plurality of Purkinje fibers 38, shown by a plurality of arrows 60, thus causing the rest of right ventricle 16 and left ventricle 18 respectively to finish contracting. In normal hearts, the electrical impulse travels simultaneously down right bundle branch 34 and left bundle branch 36 and their respective networks of Purkinje cells, thus causing both ventricles to pump and contract simultaneously. Thus, in normal healthy human hearts, the electrical impulse initiated in SA node 28 causes right atrium 12 and left atrium 14 to substantially simultaneously pump blood into right ventricle 16 and left ventricle 18 respectively and then to substantially simultaneously cause right ventricle 16 and left ventricle 18 to pump blood respectively to the lungs and body.

The electrical impulse received by AV node 30 from SA node 28 substantially overrides any natural electrical impulses AV node 30 would generate on its own. Thus once AV node 30 receives an electrical impulse from SA node 28, and after the AV delay, the pacemaker cells in AV node 30 effectively transfer the electrical impulse from SA node 28 by generating their own electrical impulse. The same is true for electrical conduction in bundle of HIS 32, right bundle branch 34, left bundle branch 36 and plurality of Purkinje fibers 38. Each time heart 50 beats, SA node 28 is substantially sending out an electrical impulse which travels through heart 50, thus causing its various chambers to contract and pump blood through the two major loops in the body as described above.

Medical conditions of the heart in general can be broken down into two major categories, those that relate to issues with the blood flow system of the heart and those that relate to issues with the electrical conduction system of the heart. Medical conditions relating to issues with the electrical conduction system of the heart are generally referred to as cardiac arrhythmias and include conditions such as tachycardia (when SA node 28 produces electrical impulses too rapidly), bradycardia (when SA node 28 produces electrical impulses too slowly), conditions where SA node 28 produces electrical impulses that have an irregular rhythm and conditions known as bundle branch block where one or both of the bundle branches in heart 50 do not conduct electrical impulses. Bundle branch block can prevent the ventricles from pumping blood altogether, leading to cardiac arrest, or can cause one ventricle to pump blood out of sync with the other ventricle, thus leading to inefficient blood circulation in the body and thus causing other health issues.

Cardiac arrhythmias are assessed by monitoring the electrical activity of the heart. This is most commonly done via electrocardiography, where a set of ten electrodes are attached to the surface of the body, primarily around the chest area where the heart is located. These electrodes are commonly referred to as surface electrodes since they monitor the electrical activity of the heart from the surface of the skin. The recordings of these electrodes produce twelve different readings of the electrical activity (usually either a measure of the current or voltage of the electrical impulses) of the heart over time, which is known as an electrocardiogram (herein abbreviated ECG). These twelve different readings are referred to as leads and are the result of different combinations of electrical signals received from each of the ten electrodes. These twelve different leads are known by the following abbreviations: V1, V2, V3, V4, V5, V6, I, II, III, aVR, aVL and aVF and can give a person skilled in the art, such as a cardiologist, a plethora of information regarding the electrical conduction system of the heart of a patient. Since the SA node of the heart sends out electrical impulses rhythmically, an ECG should produce a recurring pattern of electrical activity over time showing how electrical impulses travel through the heart. Reference is now made to FIG. 2A which is a schematic illustration of an ECG, generally referenced 70, showing the classification of various waveforms in a single electrical impulse traveling through a human heart (not shown), as is known in the prior art. ECG 70 is printed on a specialized boxed grid 71, where the horizontal (i.e., left-right) axis (not shown or labeled) represents time and the vertical (i.e., up-down) axis (not shown or labeled) represents the amplitude of electrical activity. Each box measures 1 millimeter (herein abbreviated mm) and every group of five boxes, representing 5 mm, is demarcated with a thicker line (not labeled), such that ECG 70 can be read at a resolution of 1 mm or 5 mm. Electrical activity can be represented as a voltage or a current. In FIG. 2A, electrical activity is represented as a voltage. Specialized boxed grid 71 is used to enable workers skilled in the art to easily interpret ECG 70 by merely looking at how many boxes a given part of a registered signal 81 covers in the horizontal and vertical directions. Sections 79, 92 and 94 in FIG. 2A show a legend indicating how much time each box and each group of five boxes represents in the horizontal direction and how much voltage each box and each group of five boxes represents in the vertical direction. For example, as shown in section 79, each box in the vertical direction represents a voltage of 0.1 millivolts (herein abbreviated mV) and each group of five boxes represents 0.5 mV. In section 92, each box in the horizontal direction represents 0.04 seconds, which is equivalent to 40 milliseconds (herein abbreviated ms). In section 94, each group of five boxes in the horizontal direction represents 0.2 seconds, which is equivalent to 200 ms.

Registered signal 81 represents a schematic illustration of a theoretical electrical impulse signal of a human heart over the course of one heartbeat registered by the ten electrodes of an ECG. Since the voltage amplitude is measured in the vertical direction, any sections of horizontal lines in registered signal 81 represent no electrical activity (such as a PR segment 80, as described below) in the heart whereas sections or segments that change over time in the vertical direction (such as a QRS interval 74, as described below) represent changes in electrical activity in the heart. A dotted line 87, added for emphasis, shows an arbitrary 0 volts line. As voltages can be positive or negative, electrical activity in the vertical direction can be registered above and below the 0 volts line thus representing differences in the polarity of the voltage of the electrical impulse as it travels through the heart.

Registered signal 81 represents the electrical signal of a single heartbeat and starts at a point 83 and ends at a point 85. As mentioned above, an electrical impulse is generated by the SA node and propagates through the atria of the heart. This is seen in ECG 70 as a wave 72, known in the art as a P-wave. P-wave 72 thus represents the traveling electrical impulse propagating through the atria and thus pushing blood from the atria into their respective ventricles. P-wave 72 is followed by P-R segment 80, which is a period of no electrical activity in the heart. P-R segment 80 represents the AV delay experienced in the heart where the AV node delays the propagation of the electrical signal to the bundle of HIS, thus allowing the atria to empty of blood. P-R segment 80 is followed by three waves, a wave 73, known as the Q-wave, a wave 75, known as the R-wave and a wave 77, known as the S-wave. In general, Q-wave 73, R-wave 75 and S-wave 77 are grouped together to form ORS interval 74, which is also known as the QRS complex. QRS complex 74 represents the propagation of the electrical impulse from the AV node to the bundle of HIS, down through the right and left bundle branches and into the plurality of Purkinje fibers. Thus ORS complex 74 represents the contraction of the right and left ventricles as they pump blood respectively to the lungs and body. QRS complex 74 is followed by an S-T segment 84, again during which no electrical activity is registered in the heart. Following S-T segment 84 is a wave 76, known as the T-wave, followed by a wave 90, known as the U-wave. Either side of U-wave 90 in the horizontal direction (i.e., over time) may be preceded and followed by a short period of no electrical activity. Electrical impulses are propagated through the heart by an electrochemical reaction involving calcium and potassium. Electrical charge can flow via the depolarization of a resting state of the cells of the heart. Once depolarized, the cells of the heart must repolarize in order to allow electrical charge to flow again. T-wave 76 represents the repolarization of the cells of the heart in the ventricles, whereas U-wave 90 represents the repolarization of the cells of the heart in the plurality of Purkinje fibers. U-wave 90 is not always visible in an actual ECG. Repolarization of the cells of the heart in the atria usually occurs during P-R segment 80 and is not usually registered or visible on an ECG. Repolarization electrochemically is substantially equivalent to the physical relaxation of the cells of the heart. Thus T-wave 76 and U-wave 90 respectively represent the relaxation of the ventricles and the plurality of Purkinje fibers.

After U-wave 90, another electrical impulse initiated by the SA node is expected, thus another P-wave (not shown) is expected. As shown in FIG. 2A, the time interval between a P-wave and a subsequent P-wave is known as a P-P interval 78 and substantially represents the heart rate of the heart, or the rate at which the heart is beating. Other known time intervals which are commonly used by skilled workers in the art include a P-R interval 82, measured from the start of P-wave 72 to the start of QRS complex 74, a Q-T interval 88, measured from the start of ORS complex 74 to the end of T-wave 76 and an S-T interval 86, measured from the start of S-T segment 84 to the end of T-wave 76. P-R interval 82 is substantially a measure of how much time it takes an electrical impulse to travel from the SA node, through the AV node into the bundle of HIS. Q-T interval 88 is substantially a measure of how much time it takes the ventricles to depolarize, pump blood out to the lungs and body and then repolarize before the next electrical impulse arrives.

As shown, a typical P-P interval may last about 750 ms (about three quarters of a second). Average human resting heart rates (i.e., when a person with a normal heart is not engaged in physical or strenuous activity) can vary between 60 to 100 beats per minute, translating into a range of between 600-1200 ms for an average P-P interval. A typical P-wave may last about 80 ms, a typical P-R segment may last between 50-120 ms, a typical QRS complex may last about 80-120 ms, a typical S-T segment may also last between 80-120 ms and a typical T-wave may last about 160 ms.

P-R segment 80 demarcated by a dotted ellipse 96, which is shown in an expanded view below ECG 70 in FIG. 2A. P-R segment 80 represents the AV delay in the propagation of electrical impulses received from the SA node to the bundle of HIS and is itself subdivided into three separate portions. The AV delay includes an intra-atrial conduction time 98, an AV nodal conduction time 100 and an infra-Hisian conduction time 102. Intra-atrial conduction time 98 represents the amount of time required for the electrical impulse to leave the SA node and arrive at the AV node and can last between 5-10 ms. AV nodal conduction time 100 represents the built-in delay in the AV node which slows the propagation of the received electrical impulse to the bundle of HIS, thus allowing the atria to empty of blood and the ventricles to fill with that blood. AV nodal conduction time 100 represents the bulk of P-R segment 80 and can last between 70-300 ms. Infra-Hisian conduction time 102 represents the amount of time required for the electrical impulse to leave the AV node and travel down the bundle of HIS to the right and left bundle branches and can last between 40-55 ms.

Reference is now made to FIG. 2B which shows an actual ECG of the heart of a healthy individual, generally referenced 110, as is known in the prior art. ECG 110 is shown on the specialized boxed paper described above in FIG. 2A. Clearly visible in ECG 110 are individual lines 113 in the vertical and horizontal directions demarcating individual boxes (each measuring 1 mm) as well as emphasized lines 111 in the vertical and horizontal directions demarcating groups of five boxes (in total, each group measuring 5 mm). As seen in ECG 110, the twelve different leads of the ten electrodes are laid out on three separate lines of registered electrical signals. For example, registered electrical signal 115A shows the leads of I, aVR, V1 and V4, registered electrical signal 115B shows the leads of II, aVL, V2 and V5 and registered electrical signal 115C shows the leads of III, aVF, V3 and V6. The twelve different leads, referenced as registered electrical signals 115A-115C are really twelve different readings of the same electrical impulse generated by the SA node and propagated through the heart. As can be seen from lead the heart of a healthy individual exhibits a P-wave 112, a QRS complex 114 and a T-wave 116. U-waves are visible in lead I. A P-P interval 118A is shown for lead I. In lead II, two consecutive P-P intervals 118B and 118C are shown next to one another. What stands out clearly in ECG 110 is the similar, rhythmic pattern of each P-P interval for each lead. Whereas P-P interval 118A has a different waveform (i.e., shape) from P-P intervals 118B and 118C, due to the registration of the electrical impulse of the heart by different electrodes, the waveforms of P-P intervals 118B and 118C are substantially similar. This is what a healthy human heart is supposed to look like in an ECG.

Reference is now made to FIG. 3A which is a schematic illustration of a human heart suffering from left bundle branch block, from a coronal cross-sectional view, generally referenced 130, as is known in the prior art. Heart 130 is substantially similar to heart 10 (FIG. 1A) and heart 50 (FIG. 1B), however not all major parts of heart 130 are labeled to avoid excessive reference numbers in FIG. 3A. FIG. 3A shows how the electrical conduction system of heart 130 is altered when a patient suffers from left bundle branch block (herein abbreviated BBB). Heart 130 includes an SA node 132, an AV node 136, a bundle of HIS 138, a right bundle branch 144, a left bundle branch 148, a plurality of right side Purkinje fibers 156 and a plurality of left side Purkinje fibers 158. The conduction pathway of electrical impulses from SA node 132 to AV node 136 is shown via a plurality of arrows 134. The conduction of electrical pulses from AV node 136 to bundle of HIS 138 is shown as an arrow 140.

A patient suffering from left BBB substantially has a condition in which electrical impulses originating from the SA node which propagate to the bundle of HIS do not continue down and propagate through the left bundle branch and through the left side Purkinje fibers of the heart. As shown, electrical impulses travel down right bundle branch 144, as shown by a plurality of arrows 142 and eventually into plurality of right side Purkinje fibers 156, shown by an arrow 154, However, electrical impulses do not travel left bundle branch 148 and into plurality of left side Purkinje fibers 158, as shown by crossed-through arrows 146, 150 and 152. Left BBB may present itself in patients differently. For example, an assessment of a patient with left BBB may not be able to pinpoint where along left bundle branch 148 the electrical impulses of the SA node cease to propagate. An individual may have no electrical conduction along left bundle branch 148 starting from a point 160A, just below bundle of HIS 138, starting from a point 160B or a point 160C, along various points of left bundle branch 148, or starting from a point 160D, wherein left bundle branch 148 conducts the electrical impulse however plurality of left side Purkinje fibers 158 do not. In each of these scenarios, a patient would be diagnosed with left BBB, even though in some of the scenarios, the left ventricle (not labeled) would partially pump blood to the body (not shown). Left BBB can also present itself in an individual in which electrical impulses are conducted through the left bundle branch and into the plurality of left side Purkinje fibers, however at a rate significantly slower than the rate at which electrical impulses propagate through the right bundle branch and the plurality of right side Purkinje fibers. As mentioned above, pacemaker cells in the heart can rhythmically generate electrical pulses and also propagate electrical pulses received. Therefore the left ventricle in the heart of an individual with left BBB having no electrical conduction starting from point 160A may still contract due to electrical impulses eventually propagating from right bundle branch 144 and plurality of right side Purkinje fibers 156 into the left ventricle. The left ventricle in the heart of such an individual may also contract if the pacemaker cells in left bundle branch 148, plurality of left side Purkinje fibers 158 or both produce native electrical impulses on their own. However as mentioned above, the pacemaker cells located in those parts of the heart produce electrical impulses at a rate which might be twice as slow as the rate at which SA node 132 produces electrical impulses.

In general, individuals having a condition of left BBB have a heart in which the left ventricle does not contract and pump blood to the body in sync with the right ventricle (not labeled). In addition, the left ventricle may not pump as efficiently as the right ventricle, since it may be receiving electrical impulses with a significant delay and at a significantly slower rate. Less efficient pumping translates into a lowered ejection fraction (i.e., the percent of blood pumped from a ventricle into an artery) of blood from the ventricle, which can lead to other health issues including congestive heart failure which is a condition resulting from poor cardiac output. A similar condition known as right BBB exists, in which electrical conduction may be blocked or delayed along right bundle branch 144, plurality of right side Purkinje fibers 156 or both. Left BBB is considered a more serious condition than right BBB since the right ventricle only needs to pump blood to the lungs, which are adjacent to the heart, whereas the left ventricle needs to pump blood to the entire body.

Reference is now made to FIG. 3B which shows an actual ECG of the heart of an individual having left BBB, generally referenced 170, as is known in the prior art. As seen in lead III, two consecutive P-waves 172A and 172B are visible thus forming a P-P interval 174. In comparison to lead III from ECG 110 (FIG. 2B) however, P-P interval 174 has a very different waveform than that of a healthy heart. As seen in lead aVL, P-waves 176A and 176B are not well defined, which are each respectively followed by P-R segments 178A and 178B. In addition, QRS-complexes 180A and 180B are very wide, especially the R-waves (not labeled), indicating the lag in time in electrical conduction to the left ventricle as a result of the left bundle branch block. Typically in patients with left BBB, conduction to the left ventricle is via cell-to-cell conduction starting in the right ventricle. This type of electrical conduction is much slower than electrical conduction via the specialized conduction system of the heart (as shown above in FIG. 1B, including the bundle of HIS, the right and left bundle branches and the plurality of Purkinje fibers). In left BBB, the specialized conduction system of the left side of the heart does not function properly. Electrical conduction to the left side of the heart nonetheless occurs due to slower cell-to-cell conduction which originates in the right ventricle. Myocardial cell-to-cell conduction is much slower than the specialized electrical conduction in the heart, thus explaining the wide QRS complex seen in left BBB patients.

Patients with right or left BBB can be treated by using cardiac resynchronization therapy (herein abbreviated CRT) in which a device, known as a pacemaker or artificial pacemaker, is inserted into the patient, that takes over the role of providing electrical impulses to the right bundle branch and left bundle branch. This action is referred to as pacing, since the artificial pacemaker takes over the role of a portion of the pacemaker cells in the heart. Pacemakers usually include two parts, a can and a plurality of leads. Reference is now made to FIG. 4, which is a schematic illustration of a pacemaker coupled with a heart, from a coronal cross-sectional view, generally referenced 190, for artificially pacing the heart, as is known in the prior art. As shown, a pacemaker 192 has been inserted into a patient (not shown) and is coupled with a heart 193, for artificially pacing it. Pacemaker 192 includes a can 194 and a plurality of leads 196A, 196B and 196C. Plurality of leads 196A-196C is coupled with can 194. Can 194 is usually positioned subcutaneously in the chest area of the patient. Can 194 includes a processor (not shown), a battery (not shown) and optionally at least one capacitor (not shown). The battery is used for powering the processor and providing electrical impulses (i.e., synchronization impulses) to plurality of leads 196A-196C. Some pacemakers may include an implantable cardioverter defibrillator (herein abbreviated ICD). In such pacemakers, the ICD functionality may require a high voltage electrical impulse and hence at least one capacitor can be used to serve that purpose. In these pacemakers, the battery can be used for building up a high voltage charge on the at least one capacitor. As some pacemakers may not have such an ICD function available, the at least one capacitor is not included and is thus an optional element in can 194. The processor receives measurements of the electrical activity of the heart via at least one of plurality of leads 196A-196C and decides when electrical pulses should be delivered to heart 193, how often and at what voltage.

As shown, heart 193 includes a right atrium 200, a right ventricle 204, a left atrium 210 and a left ventricle 208. Known pacemakers usually include at least three leads which are usually coupled intravascularly to the heart via the superior vena cava (not shown). A first lead, lead 196A, is positioned in right atrium 200, where the SA node (not shown) is located. A distal end 198 of lead 196A is used to sense electrical activity in right atrium 200, such as when a P-wave (not shown) was initiated by the SA node, thus indicating that right atrium 200 and left atrium 210 are contracting. Distal end 198 can also be used to send electrical impulses to right atrium 200 and left atrium 210, thus replacing the role of the SA node. A second lead, lead 196B, is positioned in right ventricle 204, usually via the tricuspid valve (not labeled), such that its distal end 202 is positioned near the plurality of Purkinje fibers (not labeled) located at the distal end of the right bundle branch. A third lead, lead 196C, is positioned in left ventricle 208. A distal end 206 of lead 196C is usually inserted into the heart via the superior vena cava into right atrium 200, and is then routed to the coronary sinus (not shown). Distal end 206 is thus shown as a dotted line. Lead 196B is used to pace right ventricle 204 and lead 196C is used to pace left ventricle 208 via the coronary sinus.

Pacemaker 192 works as follows. Lead 196A includes a sensor (not shown) for sensing atrial contractions (i.e., a P-wave) in right atrium 200 and left atrium 210. When a P-wave is detected, the sensor in lead 196A sends a signal back to the processor in can 194 indicative of the P-wave. Upon receiving the indication of the P-wave, the processor is programmed to wait a predetermined amount of time which is supposed to approximate the normal physiological AV delay of the AV node (not labeled) and then sends an electrical impulse down leads 196B and 196C to pace right ventricle 204 and left ventricle 208. The electrical impulse sent down leads 196B and 196C may be sent simultaneously or nearly simultaneously thus causing both right ventricle 204 and left ventricle 208 to contract at substantially the same time. The left BBB in the natural electrical conduction to the left bundle branch is thus bypassed by the electrical impulse sent down lead 196C, and the simultaneous or near simultaneous contraction of both right ventricle 204 and left ventricle 208 thus attempts to negate any physiological consequences of the left BBB.

Pacemaker systems and CRT methods (also referred to as pacing methods) based on the principles outlined in FIG. 4 are known in the art. In addition, cardiac resynchronization therapy methods are known in the art. For example, US Patent Application No. 2010/0087888 A1 to Maskara, entitled "Methods and apparatuses for cardiac resynchronization therapy mode selection based on intrinsic conduction" is directed to systems and methods for selecting a cardiac resynchronization therapy (CRT) mode, the selection being between a synchrony optimization mode and a preload optimization mode. The system and method involve sensing electrocardiogram (ECG) data for a patient, identifying a parameter from the sensed ECG, such as a PR interval, comparing the parameter to a threshold and selecting a CRT mode. The selected CRT mode is based on the comparison of the parameter to the threshold. The synchrony optimization mode may be selected if the parameter is less than the threshold, and may optimize CRT for fusion between a left ventricular pulse and an intrinsic wavefront. The preload optimization mode may be selected if the parameter is greater than the threshold, and may optimize CRT for fusion between respective wavefronts of the left ventricular pace and a right ventricular pace.

US Patent Application No. 2013/0035738 A1 to Karst et al. and assigned to Pacesetter, Inc., entitled "Methods and systems for determining pacing parameters based on repolarization index" is directed to methods and systems for determining pacing parameters for an implantable medical device (IMD). The methods and systems are intracardiac and provide electrodes in the right atrium (RA), right ventricle (RV) and left ventricle (LV). RV cardiac signals and LV cardiac signals are sensed at an RV electrode and an LV electrode, respectively, over multiple cardiac cycles, to collect global activation information. A T-wave in the LV cardiac signal is identified. A repolarization index is calculated based at least in part on a timing of the T-wave identified in the LV cardiac signal. At least one pacing parameter is then set based on the repolarization index. The set pacing parameter represents at least one of an AV delay, an inter-ventricular interval and an intra-ventricular interval. Optionally, the methods and systems may deliver an RV pacing stimulus at the RV electrode such that the LV cardiac signal sensed thereafter includes the RV pacing stimulus followed by a T-wave. The methods and systems determine a waveform metric such as at least one of a QT interval, T-wave duration and T-wave amplitude, and utilize the waveform metric to determine the repolarization index.

U.S. Pat. No. 8,160,700 issued to Ryu et al. and assigned to Pacesetter, Inc., entitled "Adaptive single site and multi-site ventricular pacing" is directed to methods for optimizing cardiac therapy using single site or multi-site pacing. One method includes the procedures of delivering a cardiac pacing therapy using an electrode configuration for left ventricular, single site pacing or left ventricular, multi-site pacing, measuring a series of interventricular conduction delays using the left ventricular pacing and right ventricular sensing (IVCD-LR), comparing the interventricular conduction delay values to a limit and, based on the comparison, deciding whether to change the electrode configuration for the left ventricular pacing. Another method includes the procedures of measuring a plurality of interventricular conduction delays using right ventricular pacing and left ventricular sensing wherein each interventricular conduction delay (IVCD-RL) corresponds to a different electrode configuration for a right ventricular lead, measuring a plurality of interventricular conduction delays using left ventricular pacing and right ventricular sensing wherein each interventricular conduction delay (IVCD-LR) corresponds to a different electrode configuration for the right ventricular lead, determining the shortest conduction delay, and based on the shortest conduction delay, selecting an electrode configuration for the right ventricular lead for use in right ventricular pacing.

U.S. Pat. No. 6,556,859 issued to Wohlgemuth et al. and assigned to Medtronic, Inc., entitled "System and method for classifying sensed atrial events in a cardiac pacing system" is directed to a system for classifying distinct signals sensed from an electrode of an implantable cardiac pacing system positioned within an atrium of a heart of a patient. The cardiac pacing system includes a pulse generator for generating pacing pulses and a controller for controlling the operation of a pacemaker. The method includes collecting atrial event signals consisting of P-wave signals and far field R-wave signals. An interim form factor histogram is generated based upon a form of collected atrial event signals. The interim form factor histogram includes an interim P-wave form factor histogram and an interim far field R-wave form factor histogram, each having bins of atrial event signals. A previously generated form factor histogram is weighted and combined with the interim form factor histogram to create a representative form factor histogram. The representative form factor histogram is analyzed to determine if a minimal safety margin is located between the representative P-wave form factor histogram and the representative far field R-wave form factor histogram. Atrial event signals are classified by form as either P-wave signals or far field R-wave signals based upon the representative form factor histogram.

SUMMARY OF THE DISCLOSED TECHNIQUE

The disclosed technique provides for a novel method and apparatus for providing cardiac resynchronization therapy, which overcome the disadvantages of the prior art. According to one embodiment of the disclosed technique there is thus provided a method for operating a pacemaker, including the procedures of building a database of a cardiac cycle of a patient suffering from bundle branch block, and artificially pacing a ventricle of the patient using the pacemaker according to anticipative atrioventricular (AV) delays in the database which are based on measured P-P intervals in the database. The procedure of artificially pacing the ventricle includes the sub-procedures of measuring a P-P interval of a current cardiac cycle, and in a subsequent cardiac cycle, detecting a P-wave and measuring a P-P interval of the subsequent cardiac cycle. The sub-procedures also include looking up an AV delay in the database corresponding to the measured P-P interval of the current cardiac cycle and delaying a pacing signal to the ventricle based on an entry of the AV delay in the database.

According to another embodiment of the disclosed technique there is thus provided an apparatus for artificially pacing a heart of a patient suffering from bundle branch block. The apparatus includes a power source, a processor, a plurality of sensors and a pacing electrode. The processor is coupled with the power source, the sensors and the pacing electrode. At least one of the sensors is for detecting P-waves in a cardiac cycle of the heart and at least another one of the sensors is for detecting QRS complexes in the cardiac cycle of the heart. The pacing electrode is for providing pacing signals to a ventricle in the heart suffering from the bundle branch block. The sensors are used to construct a database of the cardiac cycle of the patient, with the database being stored on the processor. The ventricle is artificially paced by the pacing electrode according to anticipative AV delays in the database which are based on measured P-P intervals in the database.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

Figure 1A:
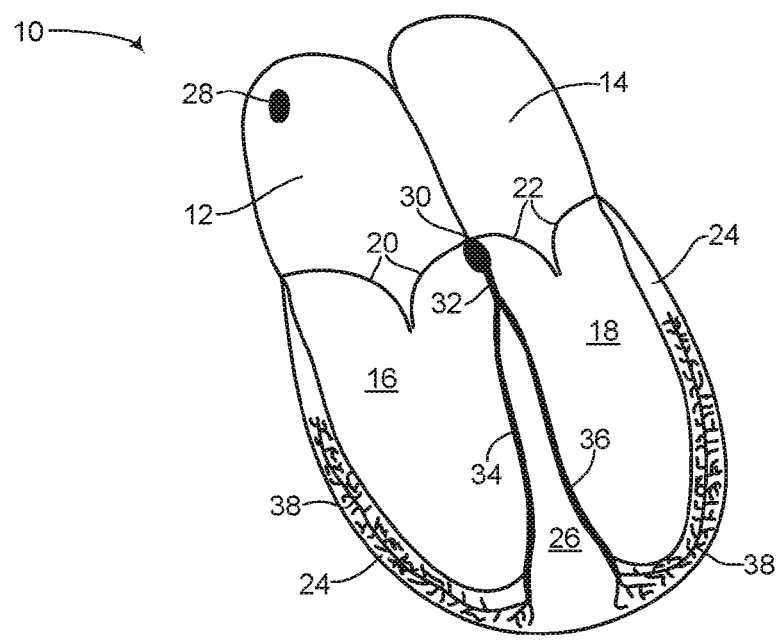
FIG. 1A is a schematic illustration of the major parts of a human heart and the electrical conduction system of such a heart, from a coronal cross-sectional view, as is known in the prior art.
Figure 1B:
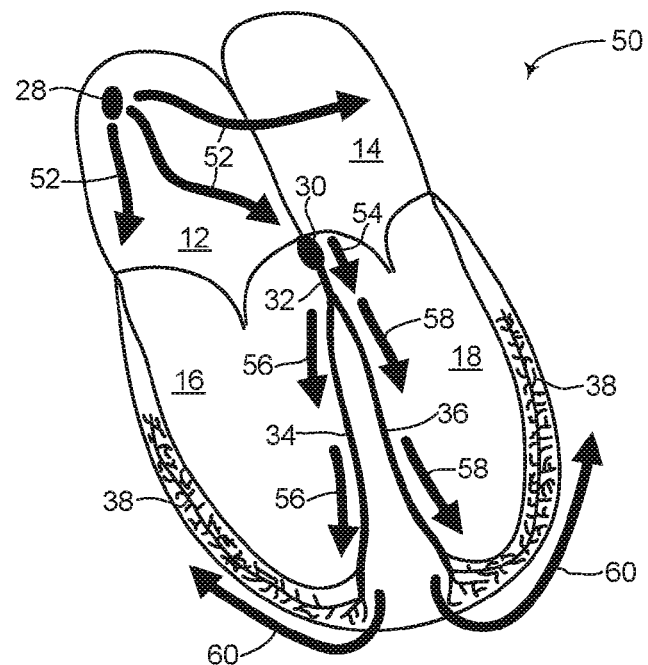
FIG. 1B is a schematic illustration of the heart shown in FIG. 1A, from a coronal cross-sectional view, showing the flow of electrical impulses through the electrical conduction system of the heart, as is known in the prior art.

The disclosed technique overcomes the disadvantages of the prior art by providing a novel method and system for providing cardiac resynchronization therapy (herein abbreviated CRT). A pacemaker employing the method of the disclosed technique builds a database of the electrical impulses of a patient suffering from bundle branch block (herein abbreviated BBB), recording values such as the time duration of a P-wave, a QRS complex and a T-wave for every P-P interval. The time delay of the intrinsically conducted AV interval (i.e., the P-R segment) for various different heart rates is also incorporated into the database. Based on the database, the pacemaker can anticipate the AV delay of a given P-P interval and deliver an electrical impulse to cause a ventricle suffering from BBB to contract in sync with the other ventricle. P-P intervals change in time duration as the heart rate varies from moment to moment. The AV interval (i.e., the AV delay) for any given heart rate also varies but in a given individual patient, at a given P-P interval, the AV interval tends to remain relatively constant from day to day for that given P-P interval. The method of the disclosed technique enables the AV delay in a pacemaker to change dynamically to match the native pumping of the heart, thus optimizing the cardiac cycle of a patient suffering from BBB. Specifically, the method of the disclosed technique enables a pacing device to build a database of intrinsically conducted AV delays (i.e., the AV delay experienced by the bundle branch which is functioning properly) and to deliver left ventricle pacing at the same time native right ventricle conduction should be occurring (or vice-versa) thus allowing for native right ventricle activation at the same time that left ventricle pacing is provided (or vice-versa). In this manner, cardiac resynchronization can be performed with the right ventricle activated via native conduction and the left ventricle being artificially paced. The disclosed technique, due to the database of individualized AV delays for all P-P intervals will thus allow for dynamic predictive cardiac resynchronization pacing wherein a pacemaker predicts when right ventricle conduction is expected to occur after a P-wave is sensed and then delivers left ventricle resynchronization pacing at substantially the same time. The method of the disclosed technique also enables a pacemaker to be programmed to deliver left ventricle pacing either sooner than or later than right ventricle activation is expected via a programmable offset in timing. This programmable offset enables a worker skilled in the art, such as a physician, to optimize the activation and synchrony of both the natively activated right ventricle and the paced left ventricle. According to the method of the disclosed technique, the database is periodically verified and modified if the recorded value of a wave for a particular time duration in a given P-P interval changes. More specifically, a pacemaker operating according to the disclosed technique will periodically wait during a given cardiac cycle (i.e., P-P interval) for the cycle to complete itself without any pacing to the left ventricle and will re-measure the native AV conduction interval (i.e., AV delay of the right ventricle) for the given P-P interval when this measurement was made. The database of AV delays built for this given patient is then updated with the new AV delay measured at the given P-P interval, This re-measurement will occur on a periodic programmed basis to allow for continuous dynamic updating of the AV delay database built for the particular patient. For example, according to the disclosed technique, the pacemaker might not pace one in every 100 heartbeats. During that P-P interval, no artificial pacing will occur and the AV delay will be re-measured. The database of AV delays may be updated for that given P-P interval if the re-measured value for the AV delay is different than the stored value for the AV delay by more than a predetermined threshold. The pacemaker operating according to the disclosed technique described herein will therefore always have a continuously up-to-date database of AV delays over a range of P-P intervals for a given patient and will thus be able to provide substantially accurate predictions of when native bundle branch conduction will occur for a given P-P interval and thus be able to deliver predictive left ventricle resynchronization pacing continuously despite ongoing changes to a patient's physiological status. The ability of the disclosed technique to look at AV delays once every 100 heartbeats will still provide a patient with appropriate resynchronization pacing for 99% of all their heartbeats. As mentioned above and described below, the disclosed technique of predictive left ventricle pacing based on AV measurements of right ventricle conduction can also be used to pace the right ventricle in a patient with a right bundle branch block through the same manner of measuring intrinsically conducted AV delays and predicting when left bundle branch conduction should occur naturally, thereby delivering right ventricle pacing at or proximate to that same point in time.

Patients who suffer from BBB usually suffer from one bundle branch not conducting electrical impulses while the other bundle branch does. In prior art pacemakers, artificial pacing is performed on both ventricles, including the ventricle which can pace naturally. The method of the disclosed technique enables artificial pacing on only the ventricle which is not pacing naturally, thus allowing the other ventricle which functions properly on its own to contract naturally. A corollary of the disclosed technique is that the battery life of a pacemaker can be significantly increased, thus reducing the number of times a patient must undergo surgery to have the battery of their pacemaker changed. This is achieved since electrical impulses are only provided to the ventricle not contracting naturally and not to both ventricles. Furthermore, according to the method of the disclosed technique, prior art pacemakers will require one less lead to be inserted into the heart, since in most cases of BBB, one ventricle functions properly. Therefore, a lead needs to be inserted into the right atrium and either into the right ventricle or the coronary sinus, depending on which ventricle is not pacing naturally.

The disclosed technique also provides for a novel system for providing CRT to a patient suffering from BBB. The system of the disclosed technique eliminates the need for leads to be inserted into the heart via a plurality of sensors placed subcutaneously around the heart and at least one electrode placed epicardially (i.e., on the surface of the heart). The plurality of sensors can sense the electrical impulses of the heart, including P-waves, T-waves and QRS complexes. The at least one electrode placed epicardially can provide an electrical impulse to artificially pace a ventricle not functioning properly. The electrode placed epicardially can also be used for sensing electrical pulses of the heart such as QRS complexes. Thus, the system of the disclosed technique can provide improved CRT by pacing a ventricle not function properly while enabling the other ventricle to pace naturally and also without having to insert any leads or electrodes in the heart or having any electrodes pass into a blood vessel leading to the heart. According to another embodiment of the disclosed technique, a single lead is placed endocardially (i.e., inside the heart) in cases where an epicardial lead cannot be placed properly for pacing the ventricle not functioning properly. In this embodiment, only a single lead is required for providing CRT as opposed to three leads in prior art pacemakers.

As explained above, the heart pumps blood to and from the lungs and to and from the body in a rhythmic, repetitive manner. The sequence via which the various parts of the heart contract and relax can be referred to as the cardiac cycle and as explained above, the cardiac cycle is regulated by electrical impulses sent from the SA node to various parts of the heart. In the art, the term 'pace' or 'pacing' is used to describe the steady rhythm each part of the heart is suppose to contract and relax at. Thus, the SA node paces the right and left atria and the right and left ventricles. Artificial pacemakers (also referred to herein as merely 'pacemakers' as opposed to the natural pacemaker of the heart, which is usually the SA node) artificially pace the heart by providing their own electrical impulse above and beyond any electrical impulses provided by the SA node or other parts of the heart. Throughout the text, the term 'electrical impulse' is used to describe the electrical impulse provided by the SA node to the heart whereas the term 'pacing signal' is used to describe the electrical impulse provided by a pacemaker to pace a ventricle of the heart not functioning properly. In addition, the term 'activation' is used interchangeably with the term 'contraction' to describe the contraction of a ventricle based on a received electrical impulse or pacing signal.

The disclosed technique is described herein with reference to an individual suffering from left BBB. As mentioned above, left BBB can be more serious and severe than right BBB, since left BBB prevents blood from circulating properly to the entire body, rather than only preventing blood from circulating properly to the lungs in the case of right BBB. There is also the case in which a patient may suffer from right BBB and left BBB. However such cases are rarer since if not treated very soon, such a block in electrical conduction of the heart may lead a patient to suffer cardiac arrest and then death. As such, even though the disclosed technique is described using the example of left BBB, it applies mutatis mutandis to patients suffering from right BBB. The required changes to the disclosed technique for treating right BBB are explained throughout the text where necessary.

As mentioned above, the left and right bundle branches in the heart provide for the simultaneous activation or contraction of the right and left ventricles. In pathological conditions, since as left BBB, a block in the electrical conduction of the electrical impulse of the SA node occurs somewhere along the left bundle branch. As mentioned above as well, left BBB can also be characterized by a retardation of the electrical impulse in the left bundle branch. In this case, even though the left bundle branch conducts the electrical impulse, it does so at a slower rate than the right bundle branch. In general, left BBB produces an abnormal cardiac physiology wherein the left ventricle contracts later and slower than the right ventricle. This leads to a lower volume of ejection fraction (i.e., cardiac output) from the left ventricle, since there is no synchrony between the left and right ventricles during ventricular systole (i.e., contraction of the ventricles). This can result in congestive heart failure since blood which is supposed to be pumped to the body may get moved back and forth between the right and left ventricles which contract at different times. As mentioned above, prior art CRT resolves the aforementioned abnormal physiology by pacing both the right ventricle and left ventricle simultaneously.

Figure 3A:
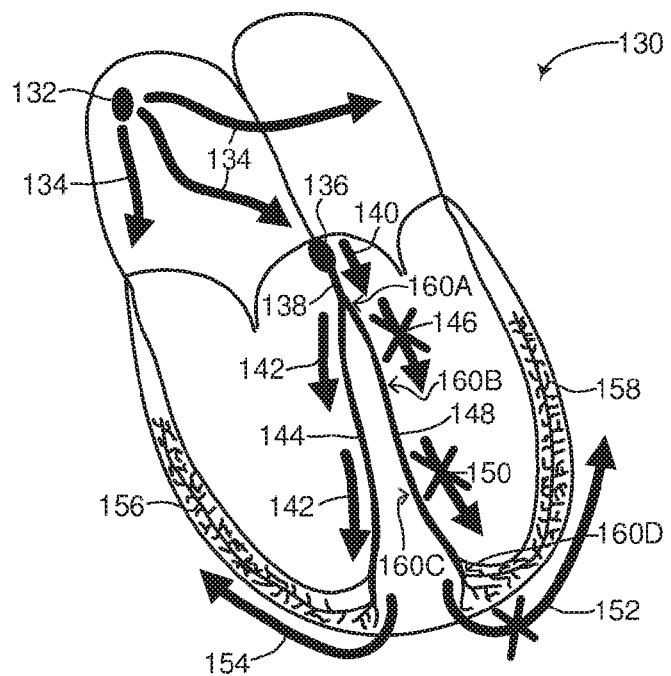
FIG. 3A is a schematic illustration of a human heart suffering from left bundle branch block, from a coronal cross-sectional view, as is known in the prior art.
Figure 3B:
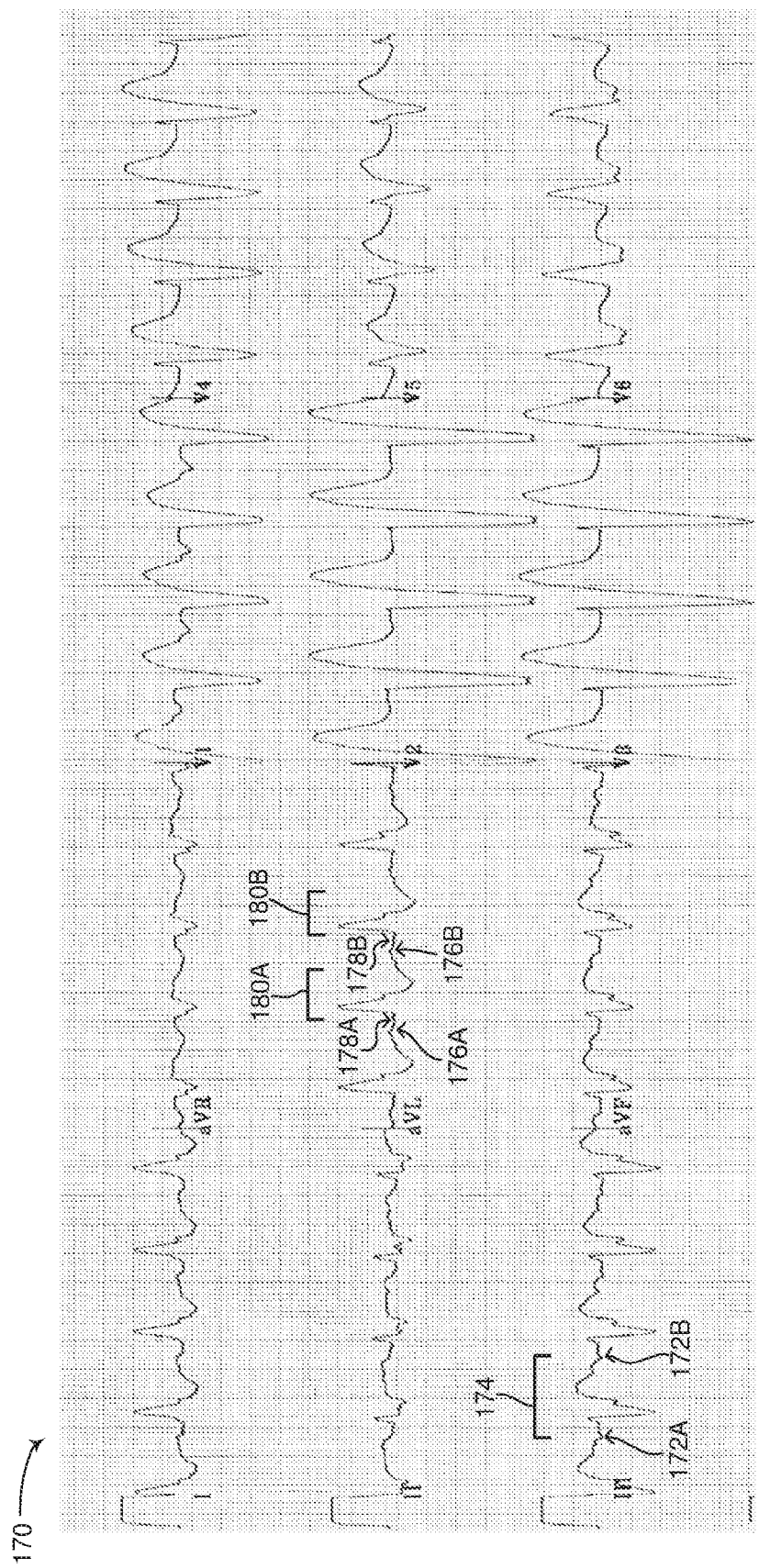
FIG. 3B shows an actual ECG of the heart of an individual having left BBB, as is known in the prior art.

The cardiac cycle in left BBB includes activation of the right and left atria, an AV delay and then activation of the right ventricle. The left ventricle will contract as well, due to the eventual spreading of the electrical impulse from the right side of the heart to the left side of the heart, however left ventricle activation will be slower than and after right ventricle activation. As shown above in FIG. 3B, the QRS complex of a person suffering from left BBB will show up on an ECG having a much wide appearance since its time duration will be longer.

Figure 2A:
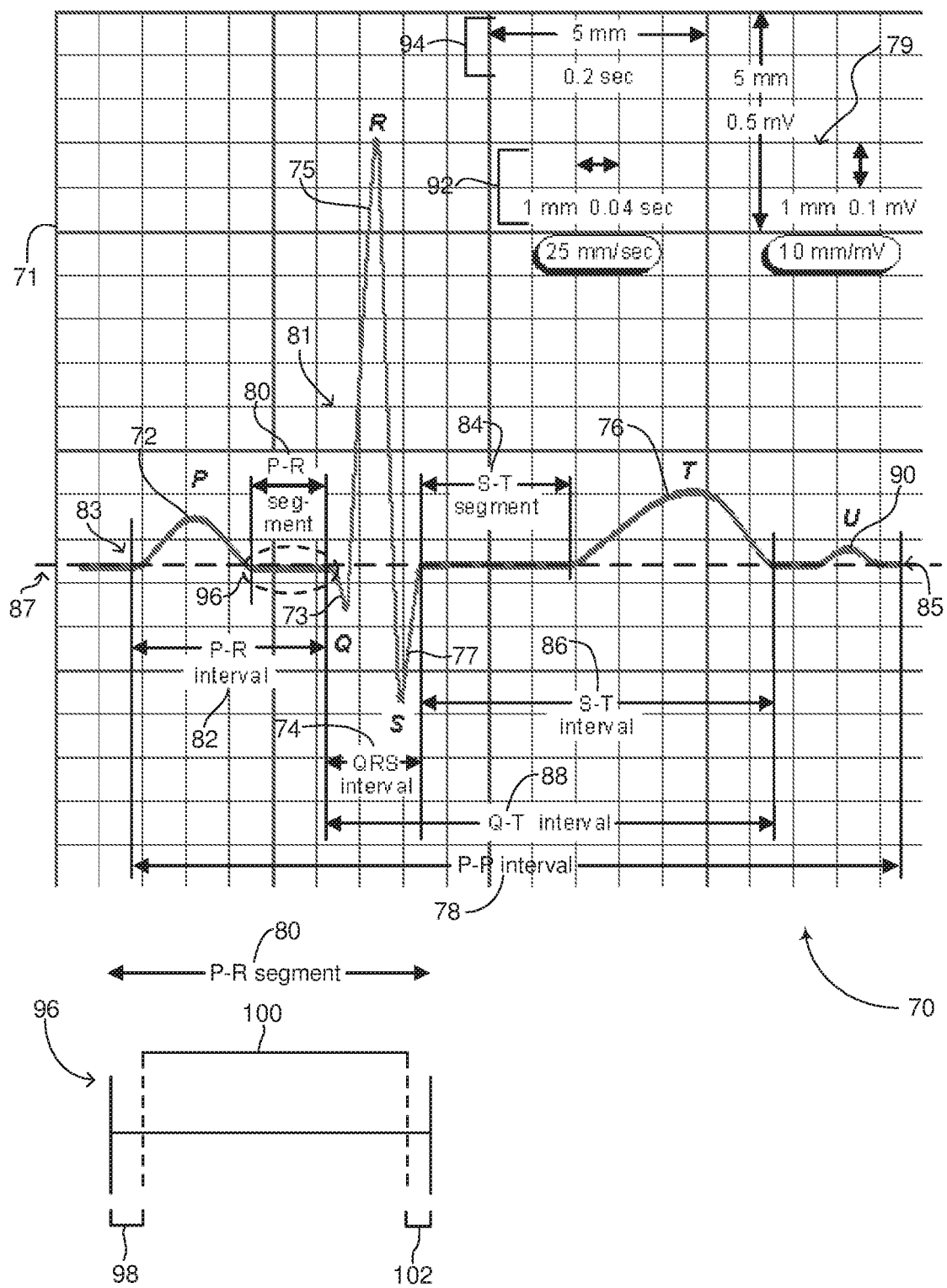
FIG. 2A is a schematic illustration of an ECG showing the classification of various waveforms in a single electrical impulse traveling through a human heart, as is known in the prior art.
Figure 2B:
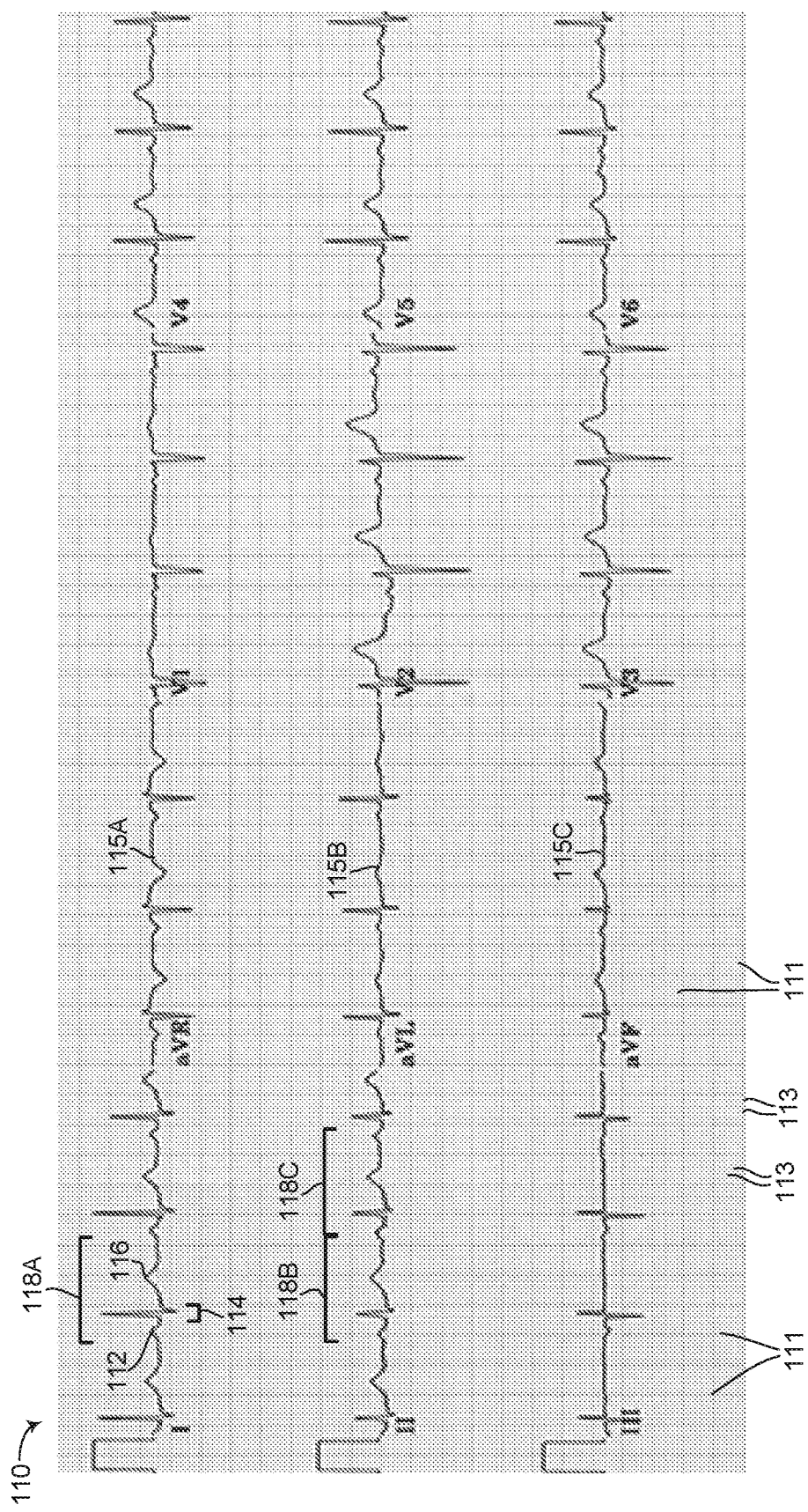
FIG. 2B shows an actual ECG of the heart of a healthy individual, as is known in the prior art.
Figure 4:
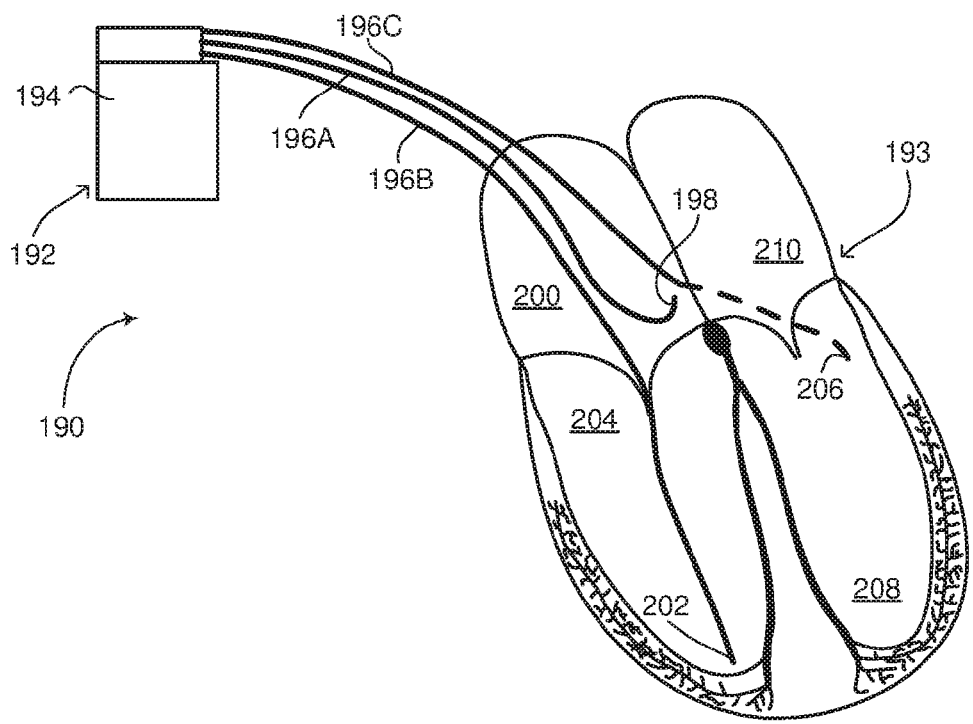
FIG. 4 is a schematic illustration of a pacemaker coupled with a heart for artificially pacing the heart, from a coronal cross-sectional view, as is known in the prior art.

As mentioned above in FIG. 2A, the P-R segment in an ECG, which represents the AV delay in the heart, includes three sub-delays known as the intra-atrial conduction time, the AV nodal conduction time and the infra-Hisian conduction time. According to the disclosed technique, an analysis of the AV delay in humans with normal and abnormal heart physiologies shows that intra-atrial conduction time and infra-Hisian conduction time are largely constant and fixed and do not significantly vary from day to day or from moment to moment (typical inter-atrial conduction time is 5-10 ms and typical infra-Hisian conduction time is 40-55 ms). However, AV nodal conduction time varies according to inputs the heart receives from the autonomic nervous system (herein abbreviated ANS). These same inputs from the ANS also control the automaticity of the SA node and thus influence the time duration of the P-P interval in the cardiac cycle. AV nodal conduction times can thus vary greatly, for example between 70-300 ms, depending on the time of day and the moment a person finds oneself in. However, since AV nodal conduction times are controlled by the same inputs the SA node receives, the variations in AV nodal conduction times are substantially related to the time duration of the P-P interval, i.e., the heart rate. According to the disclosed technique, during periods of slower heart rates, the AV nodal conduction times will tend to be longer and vice-versa, during periods of rapid heart rates, the AV nodal conduction times will be shorter. For a given individual it is thus possible to measure AV nodal conduction times at various heart rates and build a database of AV nodal conduction times for any given heart rate. This database can then be used to predict and anticipate what the AV nodal conduction time will be for any given individual at any given heart rate. Therefore, according to the disclosed technique, CRT can be applied to a patient suffering from left BBB by pacing the left ventricle according to the anticipated AV nodal conduction time for a given measured P-P interval.

Figure 5A:
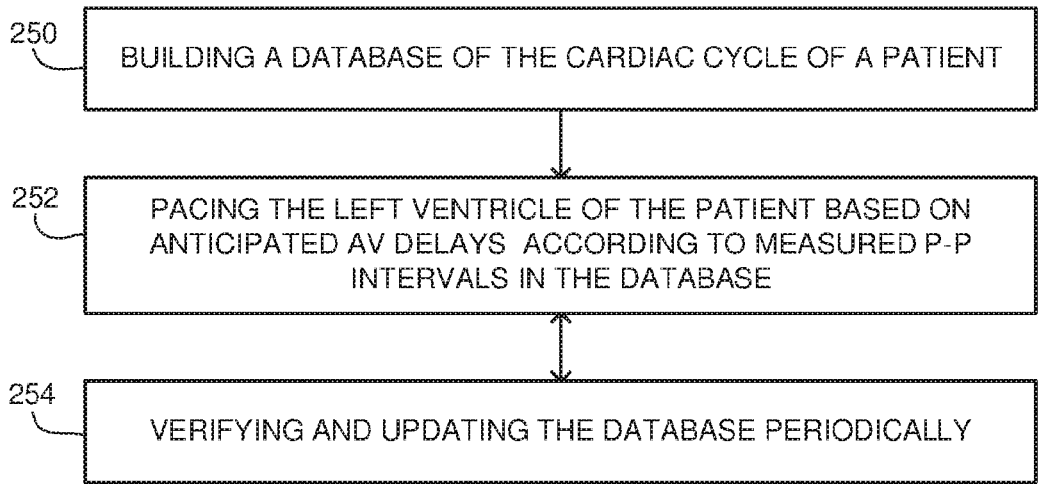
FIG. 5A is a schematic illustration of a method for cardiac resynchronization therapy using anticipated AV delays, operative in accordance with an embodiment of the disclosed technique.

Reference is now made to FIG. 5A, which is a schematic illustration of a method for cardiac resynchronization therapy using anticipated AV delays, operative in accordance with an embodiment of the disclosed technique. In a procedure 250, a database of the cardiac cycle of a patient is built. The database is built using at least two sensors. At least one sensor is used for detecting a P-wave and measuring its time duration and at least another sensor is used for detecting the corresponding QRS complex of the detected P-wave and measuring its time duration. Therefore, for each detected and measured cardiac cycle (i.e., each detected and measured heartbeat), the database will include a time stamp entry indicating the onset of a P-wave and its time duration and the onset of a QRS complex immediately following the detected P-wave and its time duration. Time stamp entries of consecutively detected P-waves will enable the database to determine and include for each P-wave detected an entry indicating the P-P interval of the detected P-wave to the next detected P-wave. In addition, the time duration of a detected P-wave and the onset of its corresponding QRS complex will enable the AV delay for a given P-P interval to be determined. Procedure 250 is executed over the course of hours or possibly even a 24-48 hour period such that it includes thousands if not tens of thousands of entries of P-P intervals and corresponding AV delays for each P-P interval.

According to one embodiment of the disclosed technique, the P-wave and the QRS complex of the cardiac cycle can be detected and the database built using an electrocardiogram. According to this embodiment, a patient is hooked up to an ECG for a period of time, such as a few hours or 1-2 days, and an ECG of the heart of the patient is recorded. Computer software can then be used to extract the relevant data from the ECG for building the database of procedure 250. According to another embodiment of the disclosed technique, a prior art pacemaker can be used to build the database of procedure 250. In this embodiment, the prior art pacemaker is implanted in the patient and the lead inserted into the right atrium is used to detect P-waves. An additional electrode may need to be used to detect each corresponding QRS complex. This additional electrode can be a subcutaneous electrode, an epicardial electrode or an intracardiac (i.e., endocardial) electrode placed near, on or in the right ventricle or left ventricle. As noted below, the same electrode used for resynchronization pacing of the left ventricle can be used to initially and periodically sense and measure the QRS complex of the cardiac cycle. In such an embodiment, the measured QRS complex of the left ventricle will occur after the native activation and QRS complex of the right ventricle. As such, an offset measurement can be subtracted from the measured ORS complex of the left ventricle to account for the delay in measuring the QRS complex of the left ventricle. For example, if the measured AV delay of the electrode placed on, in or near the left ventricle records a reading of 200 ms, conduction in the right ventricle can be predicted by approximating the width of the QRS complex measured during the left bundle branch block conduction of the patient, which should be about 80 ms. More precisely, conduction in the right ventricle can be determined by the difference between the duration of a normal QRS complex for that patient and the prolonged ORS complex seen during the left bundle branch block conduction. The AV delay therefore recorded for that P-P interval may be offset by about 80 ms or the extra conduction time introduced into the left ventricle due to the left BBB of this patient. The processor of the prior art pacemaker also needs to be reprogrammed to build a database of detected P-waves and QRS complexes as well as to then use that data to determine P-P interval time durations and corresponding AV delays. In addition, in this embodiment, the processor will also include a programmable blanking period after the detection of a QRS complex, since the lead used to detect the P-wave may not be able to differentiate between a detected P-wave and a detected T-wave. The blanking period will substantially last the average duration of a T-wave, during which the lead used to detect P-waves will refrain from registering any detected electrical impulses. The blanking period is programmable such that a worker skilled in the art, such as a cardiologist, can optimize the blanking period for a given individual while the database of procedure 250 is built. After the blanking period, this lead will then resume detecting electrical impulses and recording the detected electrical impulses at the onset of a P-wave. Besides prior art pacemakers, prior art ICDs can be used as well. In general, any existing implantable pacemaker or ICD, which can be collectively referred to as implantable heart devices, can be used to build the database in procedure 250 provided it can detect a P-P interval and an AV delay or the parameters necessary for determining the P-P interval and the AV delay of the cardiac cycle of a patient.

Figure 6:
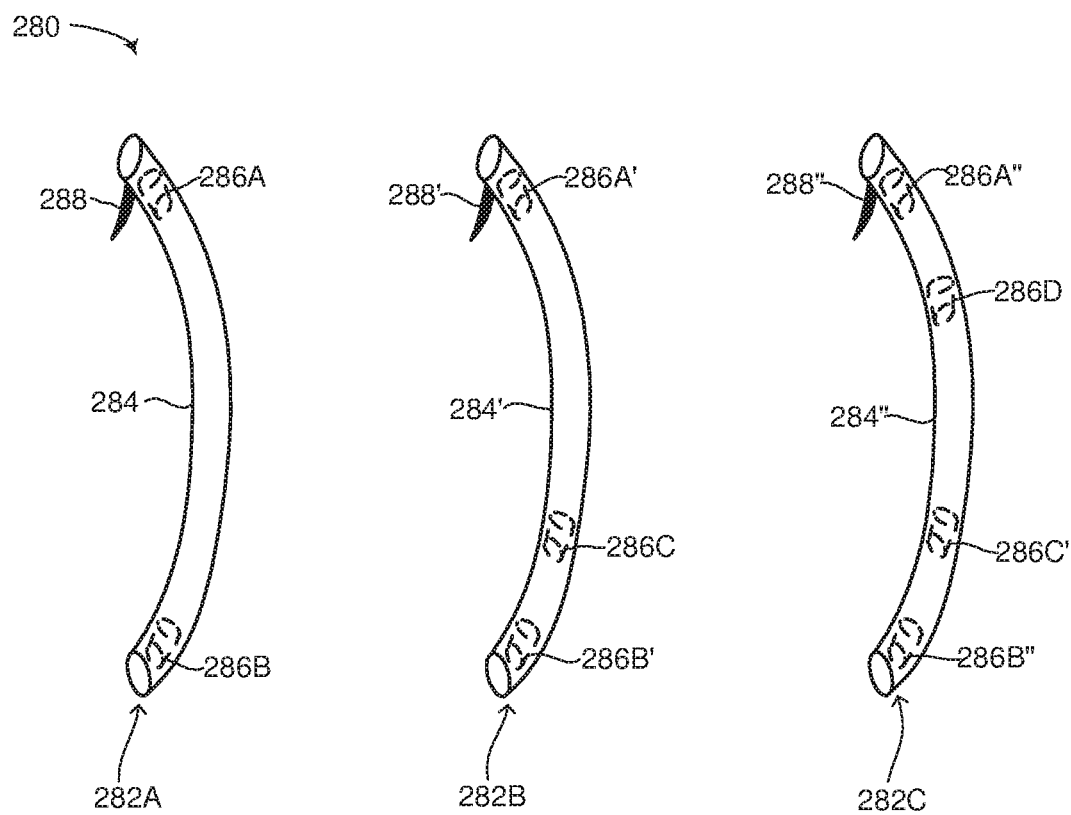
FIG. 6 is a schematic illustration of various novel pacemakers, constructed and operative in accordance with a further embodiment of the disclosed technique.

According to a further embodiment of the disclosed technique, a novel pacemaker of the disclosed technique, as described below in FIG. 6, is used to build the database in procedure 250. This novel pacemaker includes at least two electrodes, at least one for detecting P-waves and at least another one for detecting QRS complexes, as well as a processor for recording all the detected electrical impulses of the heart as data. The at least one electrode used for detecting the P-wave is placed subcutaneously near the right atrium for detecting P-waves and the at least one electrode for detecting the QRS complexes is placed either subcutaneously near the right ventricle or the left ventricle, epicardially on the surface of the heart over the right ventricle or over the left ventricle or endocardially inside the right ventricle or inside the left ventricle. As explained above, if the electrode for recording the QRS complex is placed near, on or inside the left ventricle then an offset may need to be subtracted from its measurement of the AV delay due to the fact that in left BBB, the QRS complex measured for the left ventricle will be delayed as compared to the native conduction of the right ventricle and its corresponding QRS complex. Epicardial placement of the electrode for detecting the QRS complex is less invasive. However a patient who has already undergone open heart surgery may have scarring tissue on the surface of the heart, thus preventing the placement of the electrode epicardially. In such patients, the electrode for detecting the QRS complex is placed endocardially. In this novel pacemaker, the processor may also have a built-in programmable blanking period such that the electrode used to sense P-waves does not erroneously detect a T-wave and record the onset of that electrical impulse as the onset of a P-wave.

In a procedure 252, once the database of procedure 250 has been built, a pacemaker implanted in a patient with the database of procedure 250 is used to pace the left ventricle. In this procedure, a P-P interval is measured by an electrode or lead. In a subsequent cardiac cycle, the processor of the pacemaker looks up the AV delay corresponding to the measured P-P interval of the previous cardiac cycle. After a P-wave is detected, the pacemaker will wait the AV delay of the corresponding measured P-P interval before delivering a pacing signal to the left ventricle. It is noted that this AV delay is anticipated based on the database of procedure 250. Therefore, in procedure 252, the pacing of the left ventricle (i.e., the CRT provided to the left ventricle) is based on the anticipated AV delays according to the measured P-P intervals in the database. Procedure 252 is explained in greater detail below in FIG. 5B. If the database of procedure 250 was constructed using an ECG, then in procedure 252, the database must be uploaded to a pacemaker, either a prior art pacemaker or the novel pacemaker of the disclosed technique, which must in turn be implanted or inserted into a patient. If the database of procedure 250 was constructed from a reprogrammed prior art pacemaker, then when the pacemaker is implanted in a patient, only two leads need to be implanted, a first lead in the right atrium for detecting a P-wave and a second lead in the coronary sinus for pacing the left ventricle. Unlike the prior art, according to this method of the disclosed technique, a prior art pacemaker can apply CRT to a patient suffering from left BBB by only pacing the left ventricle and thus only requiring two leads. No leads therefore need to be placed in the right ventricle. If the database of procedure 250 was constructed from the novel pacemaker of the disclosed technique, then when the pacemaker is inserted into a patient, only a single lead or electrode needs to be inserted into the heart (if the electrode is placed endocardially) or on the heart (if the electrode is placed epicardially) in order to deliver a pacing signal. The sensor for detecting P-waves in the novel pacemaker of the disclosed technique is merely placed subcutaneously near the heart for detecting P-waves in the right atrium. Thus according to the disclosed technique, CRT can be applied to a patient suffering from left BBB using only a single lead or electrode for providing pacing signals to the left ventricle. That same single lead or electrode can also be used for periodically measuring and detecting the QRS complex of the left ventricle and can be used to update the database of procedure 250, as explained below in procedure 254. It is noted as well that any known implantable 100, pacemaker or existing epicardial pacing lead or endocardial pacing lead can be used with the disclosed technique to provide the CRT by pacing the left ventricle according to the AV delay in the database.

It is noted that during a given cardiac cycle, the at least one electrode measuring a P-wave also measures the current P-P interval such that for the subsequent cardiac cycle, the AV delay will be optimized to match its corresponding P-P interval in the database. Therefore, as the P-P interval measured by the pacemaker changes, the AV delay waited by the pacemaker before providing the pacing signal to the left ventricle also changes. In prior art pacemakers, the AV delay is a programmable function, however once set for a given pacemaker, remains fixed and constant unless the function is reprogrammed by a cardiologist or worker skilled in the art. In the disclosed technique, the AV delay varies dynamically with changes in the measured P-P interval. This dynamically changed delay is also updated on an ongoing dynamic basis by a pacemaker operating according to the methods described in FIGS. 5A and 5B by periodically again measuring intrinsically conducted AV delays at various P-P intervals (this is described below in more detail in procedure 254). Recall that the average resting heartbeat (i.e., P-P interval) of an adult human ranges from 70 to 100 beats per minute. Therefore, according to the disclosed technique, the AV delay of a pacemaker functioning according to the method of FIG. 5A may change tens of times every minute.

Figure 5B:
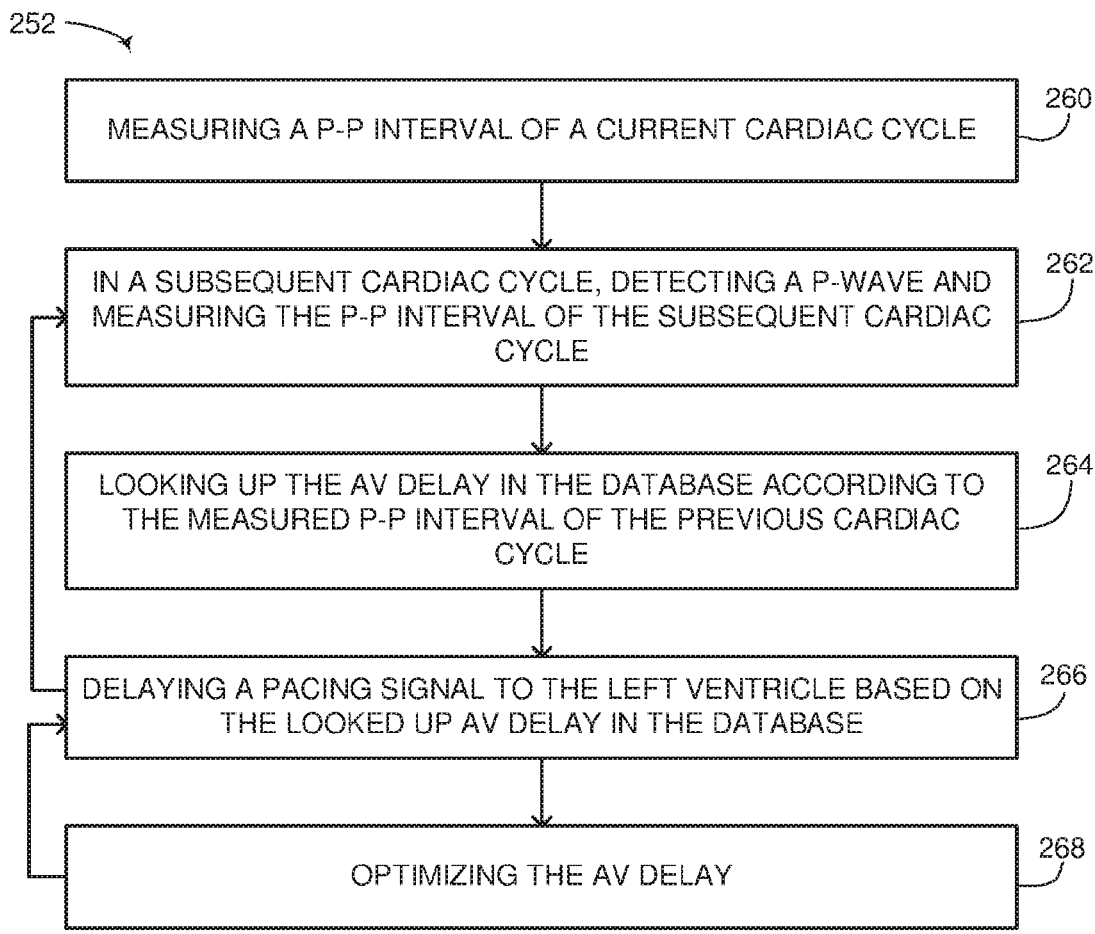
FIG. 5B is a schematic illustration of the sub-procedures of procedure 252 from FIG. 5A, for pacing a left ventricle using anticipated AV delays, operative in accordance with another embodiment of the disclosed technique.

Reference is now made to FIG. 5B, which is a schematic illustration of the sub-procedures of procedure 252 from FIG. 5A, for pacing a left ventricle using anticipated AV delays, operative in accordance with another embodiment of the disclosed technique. In a sub-procedure 260, a P-P interval of a current cardiac cycle is measured. As mentioned above in FIG. 5A, the P-P interval can be measured using at least one electrode of a prior art pacemaker or of a novel pacemaker according to the disclosed technique. In a sub-procedure 262, in a subsequent cardiac cycle (i.e., the next cardiac cycle), the P-wave is detected and the P-P interval of this subsequent cardiac cycle is also measured. The detection of the P-wave includes detecting its onset as well as its time duration. In this respect, the end of a P-wave is known to the pacemaker. In a sub-procedure 264, the AV delay in the database corresponding to the measured P-P interval of the previous cardiac cycle, which was measured in sub-procedure 260, is determined by looking up its corresponding value in the database of procedure 250 (FIG. 5A). In a sub-procedure 266, a pacing signal to the left ventricle is delayed based on the entry for the AV delay in the database. After the P-wave has been detected in sub-procedure 262 and has ended, the pacemaker delays the application of a pacing signal to the left ventricle according to the AV delay listed in the database for the measured P-P interval of the previous cardiac cycle. After sub-procedure 266, the method returns to sub-procedure 262, where for the next cardiac cycle, the P-wave is detected and the P-P interval of that next cardiac cycle is measured. Thus in sub-procedures 264 and 266, the AV delay looked up and applied to the pacemaker is always based on the measured P-P interval of the previous cardiac cycle.

In sub-procedure 266, the AV delay applied to the pacemaker may be the AV delay listed in the database. Therefore, if a particular P-P interval measured 1.1 seconds and the AV delay for that P-P interval was determined to be 150 ms, then when the end of the P-wave in sub-procedure 262 has been detected, the pacemaker will wait 150 ms before pacing the left ventricle. It is noted however that when the database was built in procedure 250 (FIG. 5A), the AV delay recorded and determined represents the time from which the P-wave ended until the time at which the QRS complex began. The actual time the QRS complex began as recorded by an electrode may not exactly match the precise time at which right ventricle activation occurs. Therefore in sub-procedure 266, if the left ventricle is paced according to the value listed in the AV delay for a particular P-P interval, the left ventricle may in actuality be activated slightly after the right ventricle is activated, thus not achieving simultaneous activation of both the right and left ventricles. In sub-procedure 268, the AV delay applied to the pacemaker for pacing the left ventricle may be optimized to increase the likelihood of simultaneous right ventricle and left ventricle pacing. Sub-procedure 268 is thus an optional sub-procedure. According to one embodiment, a fixed decrease in the delay recorded in the AV delay field in the database may be applied to the delay used in sub-procedure 266. For example, the fixed decrease in delay may be between 10 to 70 ms and may be a programmable or adjustable feature which a worker skilled in the art can set in a pacemaker placed in a patient. Using the example above, even though the AV delay for a given P-P interval may be 150 ms, the delay actually applied to the pacemaker before pacing the left ventricle may be 110 ms if the fixed decrease in delay is 40 ms. The fixed decrease in delay, as explained above, is to account for the slight difference in time between when right bundle branch conduction occurred and the right ventricle contracted and when the QRS complex was detected and measured by an electrode when the database was built. According to another embodiment of the disclosed technique, echocardiographic parameters, hemodynamic parameters, or both, can be used to modify the delay applied by the pacemaker to the pacing signal for the left ventricle in sub-procedure 266. The modification may either result in an increase or a decrease in the delay applied to the predictive pacing signal for the left ventricle. Echocardiographic parameters and hemodynamic parameters can be determined via known medical imaging techniques, such as an echocardiogram, an angiogram and the like. After sub-procedure 268, the method returns to sub-procedure 266. Sub-procedure 268 may be performed at regular intervals, such as once every couple of months, or each time a patient visits their cardiologist for a routine check-up.

Thus according to the sub-procedures of FIG. 5B, the cardiac cycle of an individual with a pacemaker operative according to the disclosed technique begins with a P-wave (activation of the right and left atria), followed by a natural AV delay, then followed by natural right bundle branch conduction and native (i.e., natural) right ventricle contraction. As the right ventricle contracts, the left ventricle will be activated according to a pacing signal applied by the pacemaker using the anticipative, and possibly optimized, AV delay described above. The disclosed technique thus allows for CRT of the left ventricle while enabling native right bundle branch conduction and native right ventricle activation. As described in more detail below, the novel pacemaker of the disclosed technique can apply CRT to the left ventricle using either one intravascular (i.e., endocardial) electrode or no intravascular electrode at all (i.e., in the case of an epicardially placed electrode). Since only the left ventricle is paced using the pacemaker of the disclosed technique, the battery life of such a pacemaker (whether a prior art pacemaker or the novel pacemaker of the disclosed technique) is significantly increased since the right ventricle does not need to be paced artificially each time the left ventricle is paced artificially. Furthermore, the optimization of the AV delay in sub-procedure 268 may be used to further delay the AV delay, thus allowing for concealed native left bundle branch conduction before artificial pacing of the left ventricle is applied. In prior art pacemakers, bi-ventricular pacing is applied to both the right and left ventricles before either the right or left ventricles pace on their own, thus preventing any native ventricle activation. Any concealed native left bundle branch conduction is thus prevented or at least minimized in prior art pacemakers. According to the disclosed technique, the left ventricle of a patient suffering from left BBB may still activate naturally (known as concealed native left bundle branch conduction), however it may be slightly delayed or weak in comparison to the right ventricle activation. The disclosed technique enables concealed native left bundle branch conduction to occur (depending on the optimization of the AV delay in sub-procedure 268), as well as native right ventricle activation. In general, native ventricle activation is more beneficial to a patient than artificial ventricle activation.

Reference is now made back to FIG. 5A. Procedure 252 is applied as long as a pacemaker functions inside a patient and is based upon the database built in procedure 250. In a procedure 254, the database built in procedure 250 is verified and updated (if necessary) periodically, to ensure that the corresponding AV delays listed in the database, per P-P interval, are indeed accurate for a given individual. The database is updated in order to maximize native right ventricle activation and the synchrony of left and right ventricle activation. Periodically can be at a predetermined time interval, such as every minute, every hour, every day, or after a predetermined number of occurrences, such as after 100 heartbeats, 500 heartbeats, 1000 heartbeats, and the like. After a predetermined time interval or a predetermined number of occurrences, the AV delay applied to the electrode used for pacing the left ventricle is extended until the QRS complex of the current P-wave is detected, at which point the pacing signal to the left ventricle is provided. According to another embodiment, when the AV delay is extended to therefore detect the time interval of the AV delay based on the actual QRS complex time duration at a given PP interval, no pacing signal may be given for that PP interval. Pacing signals are then resumed in subsequent cardiac cycles until the next predetermined time interval or predetermined number of occurrences. The time at which the QRS complex is detected can be used to determine an on-the-fly determination of the current AV delay. This determined current AV delay can then be compared to the AV delay listed in the database for the current PP interval. If the two AV delays are different by more than a predefined threshold, the AV delay listed in the database is updated to the AV delay determined on-the-fly. The AV delay entry in the database may either be written over with the updated AV delay, or an update value (either positive or negative) may be appended to the AV delay entry in the database to adjust the entry to match the determined on-the-fly AV delay. This ensures that the pacemaker is providing the anticipated left ventricle pacing signal at the correct time during the cardiac cycle to maximize the likelihood of simultaneous right and left ventricle activation. Procedure 254 is executed often such that the database of procedure 250 remains dynamic and accurate.

As mentioned above, FIGS. 5A and 5B were described for an individual suffering from left BBB. The methods of the disclosed technique described above can be applied to an individual suffering from right BBB by reversing the placement of the electrode used for pacing the left ventricle onto the right ventricle. In such an embodiment, a database is constructed based on the native activation of the left ventricle and the AV delays in the database are used to pace the right ventricle. Anticipative right ventricle pacing according to the disclosed technique, as described above, may help patients suffering from pulmonary hypertension, right sided heart failure and tricuspid valve regurgitation.

Reference is now made to FIG. 6 which is a schematic illustration of various novel pacemakers, generally referenced 280, constructed and operative in accordance with a further embodiment of the disclosed technique. FIG. 6 shows three embodiments of the novel pacemaker of the disclosed technique, labeled as 282A, 282B and 282C. A pacemaker 282A includes an elongated body 284. Elongated body 284 may have a cylindrical, tubular or polygonal cross-section (not shown). Elongated body 284 houses a battery (not shown), a processor (not shown), a plurality of sensors 286A and 286B and a pacing electrode 288. The battery is coupled with the processor, pacing electrode 288 and the plurality of sensors 286A and 286B. Pacing electrode 288 has a tooth-like shape and can be inserted epicardially on the surface of a heart (not shown). The processor is programmed to operate using the methods described above in FIGS. 5A and 5B. Plurality of sensors 286A and 286B are surface sensors designed to sense the electrical activity of the heart subcutaneously. Plurality of sensors 286A and 286B are respectively placed at the distal and proximal ends of pacemaker 282A. Sensor 286A is used for detecting QRS complexes and sensor 286B is used for detecting P-waves. Plurality of sensors 286A and 286B can be used to build a database of P-P intervals and corresponding AV delays. In addition, sensor 286B can be used for detecting P-waves which the processor will use to determine when to send a pacing signal or pacing indication to pacing electrode 288. Pacing electrode 288 is a single electrode used to provide pacing signals to the heart. Two other embodiments of the pacemaker of FIG. 6 are shown. Pacemaker 282B includes elements substantially similar to pacemaker 282A, such as an elongated body 284, a pacing electrode 288 and a plurality of sensors 286A', 286B' and 286C. Pacemaker 282C includes elements substantially similar to pacemakers 282A and 282B, such as an elongated body 284", a pacing electrode 288" and a plurality of sensors 286A", 286B", 286C' and 286D. Pacemakers 282A, 282B and 282C merely differ in the number of sensors they include. Whereas pacemaker 282A includes a minimal number of sensors for detecting P-waves and QRS complexes, pacemakers 282B and 282C include additional sensors to allow for finer discrimination of P-wave activity. Sensors for detecting electrical activity of the heart subcutaneously may erroneously detect other electrical activity subcutaneously such as skeletal myopotentials or extra-cardiac noise. By increasing the number of sensors used to detect P-wave activity, skeletal myopotential noise is substantially eliminated in detecting P-waves. For example, since myopotential noise is often random and is generated from multiple muscle groups, a plurality of sensors all recording at once enable a more precise and clear detection of P-waves as such random noise seen on one sensor would be coming most likely from a muscle group near that sensor. This same noise would not be expected to be recorded at the same level at a sensor still close to the heart but further removed from the muscle group causing the noise. This noise can then be eliminated when detecting P-waves.

It will be appreciated by persons skilled in the art that the disclosed technique is not limited to what has been particularly shown and described hereinabove. Rather the scope of the disclosed technique is defined only by the claims, which follow.

The invention claimed is:

1. Method for operating a subcutaneous pacemaker, comprising the procedures of:
   building a database of a cardiac cycle of a patient suffering from bundle branch block, said database comprising time stamped entries indicating an onset of a P wave and a time duration of said P wave of said cardiac cycle and an onset of a QRS complex and a time duration of said QRS complex of said cardiac cycle immediately following said P wave, said database being built using at least two subcutaneous sensors for sensing said onset and said time duration of said P wave and said onset and said time duration of said QRS complex;
   determining atrioventricular (AV) delays of said cardiac cycle corresponding to measured P-P intervals of said cardiac cycle based on said time duration of said P wave and said onset of said QRS complex, said AV delays being stored in said database; and
   artificially pacing a first ventricle of said patient suffering from bundle branch block using said pacemaker according to said AV delays in said database, thereby enabling native activation of a second ventricle of said patient not suffering from bundle branch block and thereby also anticipating a correct time during said cardiac cycle to pace said first ventricle to maximize a likelihood of simultaneous activation of said first ventricle and said second ventricle.

2. The method according to claim 1, wherein at least one of said at least two sensors detects at least one P wave of said cardiac cycle and measures a time duration of said at least one P wave and wherein at least another one of said at least two sensors detects at least one QRS complex corresponding to said detected at least one P wave and measures a time duration of said at least one QRS complex.

3. The method according to claim 1, further comprising the procedure of determining said measured P-P intervals for each said P wave and a next detected P wave.

4. The method according to claim 1, wherein said procedure of building said database is executed over the course of a plurality of hours.

5. The method according to claim 1, wherein said procedure of building said database is executed using an electrocardiogram and computer software.

6. The method according to claim 1, further comprising the procedure of subtracting an offset measurement from each respective corresponding QRS complex detected in said cardiac cycle.

7. The method according to claim 6, wherein said offset measurement accounts for a delay in detecting each said respective corresponding QRS complex in said first ventricle in said patient.

8. The method according to claim 1, further comprising the procedure of adding a blanking period to said at least one sensor for detecting P waves.

9. The method according to claim 8, wherein said blanking period is programmable.

10. The method according to claim 8, wherein said blanking period substantially lasts an average duration of a T wave in said cardiac cycle.

11. The method according to claim 1, wherein said procedure of building said database is executed using a subcutaneous heart device comprising said at least two subcutaneous sensors, wherein a first one of said at least two subcutaneous sensors is a first electrode placed subcutaneously near a right atrium of said patient for detecting P waves in said cardiac cycle and wherein a second one of said at least two subcutaneous sensors is a second electrode for detecting respective corresponding QRS complexes in said cardiac cycle.

12. The method according to claim 11, wherein said second electrode is placed in said patient subcutaneously near said ventricle.

13. The method according to claim 11, further comprising the procedure of subtracting an offset measurement from each respective corresponding QRS complex detected in said cardiac cycle.

14. The method according to claim 11, wherein said procedure of artificially pacing said ventricle is executed using said at least one additional electrode.

15. The method according to claim 14, wherein said at least one additional electrode is placed in said patient epicardially on a surface of the heart of said patient over said ventricle.

16. The method according to claim 1, wherein said procedure of artificially pacing said first ventricle comprises the sub procedures of:
 measuring a P-P interval of a current cardiac cycle;
 in a subsequent cardiac cycle, detecting a P wave and measuring a P-P interval of said subsequent cardiac cycle;
 looking up an AV delay in said database corresponding to said measured P-P interval of said current cardiac cycle; and
 delaying a pacing signal to said first ventricle based on an entry of said AV delay in said database.

17. The method according to claim 16, wherein said sub procedure of measuring said P-P interval comprises detecting said onset of said P wave and a time duration of said P-P interval.

18. The method according to claim 16, wherein said procedure of artificially pacing said first ventricle comprises a further sub procedure of optimizing said AV delay.

19. The method according to claim 18, wherein said sub procedure of optimizing comprises applying a fixed decrease to said entry of said AV delay in said database.

20. The method according to claim 19, wherein said fixed decrease is adjustable.

21. The method according to claim 18, wherein said entry of said AV delay in said database is modified based on at least one parameter.

22. The method according to claim 21, wherein said at least one parameter is selected from the list consisting of:
 echocardiographic parameters; and
 hemodynamic parameters.

23. The method according to claim 21, wherein said modification of said AV delay results in an increase in said entry of said AV delay.

24. The method according to claim 21, wherein said modification of said AV delay results in a decrease in said entry of said AV delay.

25. The method according to claim 18, wherein said sub procedure of optimizing is performed at regular intervals.

26. The method according to claim 16, wherein said sub procedure of delaying said pacing signal allows for concealed native bundle branch conduction of said first ventricle before said pacing signal is applied.

27. The method according to claim 1, further comprising the procedure of verifying and updating said database periodically.

28. The method according to claim 27, wherein periodically is at a predetermined time interval.

29. The method according to claim 27, wherein periodically is after a predetermined number of occurrences.

30. The method according to claim 27, wherein said procedure of verifying and updating comprises the sub procedure of extending an AV delay in a pacing signal to said first ventricle based on an entry of said AV delay in said database until a QRS complex of a current P wave is detected.

31. The method according to claim 30, wherein said procedure of verifying and updating further comprises the sub procedures:
 not providing said pacing signal when said AV delay is extended;
 determining a current AV delay on the fly based on said detected QRS complex; and
 comparing said current AV delay to said entry of said AV delay.

32. The method according to claim 31, wherein said entry of said AV delay in said database is updated to said current AV delay determined on the fly if said entry of said AV delay in said database and said current AV delay determined on the fly are different by more than a predetermined threshold.

33. The method according to claim 1, wherein said bundle branch block is selected from the list consisting of:
 left bundle branch block; and
 right bundle branch block.

34. The method according to claim 1, wherein each one of said AV delays represents a time period said pacemaker waits after detecting a P wave before said procedure of artificially pacing said first ventricle.

35. Subcutaneously positionable apparatus for artificially pacing a heart of a patient suffering from bundle branch block, comprising:
 a power source;
 a processor, coupled with said power source;
 a plurality of subcutaneous sensors, coupled with said processor, at least one of said plurality of subcutaneous sensors for detecting P waves in a cardiac cycle of said heart and at least another one of said plurality of subcutaneous sensors for detecting QRS complexes in said cardiac cycle of said heart; and
 a pacing electrode, coupled with said processor, for providing pacing signals to a first ventricle in said heart suffering from said bundle branch block;
 wherein said plurality of subcutaneous sensors are used to construct a database of said cardiac cycle of said patient, said database being stored on said processor, said database comprising time stamped entries indicating an onset of said P waves and a time duration of said P waves of said cardiac cycle and an onset of said QRS complexes and a time duration of said QRS complexes of said cardiac cycle immediately following said P wave, said database further comprising atrioventricular (AV) delays of said cardiac cycle corresponding to measured P-P intervals of said cardiac cycle determined from said time duration of said P waves and said onset of said QRS complexes, said AV delays being stored in said database; and wherein said first ventricle is artificially paced by said pacing electrode according to said AV delays in said database, thereby enabling native activation of a second ventricle in said heart not suffering from said bundle branch block and thereby also anticipating a correct time during said cardiac cycle to pace said first ventricle to maximize a likelihood of simultaneous activation of said first ventricle and said second ventricle.

36. The apparatus according to claim 35, wherein said apparatus has an elongated body.

37. The apparatus according to claim 36, wherein said elongated body has a cross section selected from the list consisting of:
cylindrical;
tubular; and
polygonal.

38. The apparatus according to claim 35, wherein said pacing electrode has a tooth like shape.

39. The apparatus according to claim 35, wherein said pacing electrode is coupled epicardially to said heart.

40. The apparatus according to claim 35, wherein said at least one of said plurality of subcutaneous sensors and said at least another one of said plurality of subcutaneous sensors are positioned at opposite ends of said apparatus.

41. The apparatus according to claim 35, wherein said processor provides a pacing indication to said pacing electrode to provide said pacing signals to said first ventricle based on said detected P waves by said at least one of said plurality of subcutaneous sensors.

42. The apparatus according to claim 35, wherein said plurality of subcutaneous sensors is used for substantially eliminating myopotential noise when detecting said P waves.

43. The apparatus according to claim 35, wherein each one of said AV delays represents a time period said pacing electrode waits after said at least one of said plurality of subcutaneous sensors detects a P wave before providing said pacing signals to said first ventricle.

* * * * *